United States Patent [19]

Lin

[11] Patent Number: 4,620,949

[45] Date of Patent: Nov. 4, 1986

[54] PROCESS FOR AMIDOCARBONYLATION OF CYCLIC AMIDES

[75] Inventor: Jiang-Jen Lin, Round Rock, Tex.

[73] Assignee: Texaco Inc., White Plains, N.Y.

[21] Appl. No.: 720,229

[22] Filed: Apr. 5, 1985

[51] Int. Cl.[4] ................ C07D 401/06; C07D 403/06; C07D 223/10

[52] U.S. Cl. .................................... 540/525; 546/188; 546/243; 548/524; 548/551; 540/451; 540/531; 540/533

[58] Field of Search ................ 260/239.3 R; 546/188, 546/243; 548/524, 551

[56] References Cited

U.S. PATENT DOCUMENTS

| 3,037,001 | 5/1962 | Becke et al. | 260/239.3 R |
| 3,157,641 | 11/1964 | Walles et al. | 260/239.3 R |

FOREIGN PATENT DOCUMENTS

| 1074045 | 1/1960 | Fed. Rep. of Germany ... 260/239.3 R |
| 2017397 | 11/1971 | Fed. Rep. of Germany ... 260/239.3 R |

OTHER PUBLICATIONS

J. Liebigs, "Ann. der Chem", vol. 755, pp. 163–170 (1972), (Witte et al.).
"Chem Berichte", vol. 40, pp. 2831–2842 (1907), (Tafel et al.).

*Primary Examiner*—Robert T. Bond
*Attorney, Agent, or Firm*—Jack H. Park; Kenneth R. Priem; Cynthia L. Kendrick

[57] ABSTRACT

Amino acid derivatives are synthesized by reacting paraformaldehyde, cyclic amides and synthesis gas with a bimetallic catalyst comprising a rhodium-containing compound and a cobalt-containing compound, optionally in the presence of a solvent at a pressure of at least 500 psi and a temperature of at least 50° C. The novel amino acid products may be hydrolyzed to amino dicarboxylic acids or used as monomers to polyamides.

15 Claims, No Drawings

PROCESS FOR AMIDOCARBONYLATION OF CYCLIC AMIDES

CROSS-REFERENCE TO RELATED APPLICATION

This application is related to U.S. patent application Ser. Nos. 06/720,228, 06/720,249, 06/720,248, 06/720,227 and 06/720,226 filed Apr. 5, 1985.

FIELD OF THE INVENTION

This invention relates to the amidocarbonylation of cyclic amides with paraformaldehyde and synthesis gas to yield amino acid derivatives and bis-amide derivatives.

More particularly this invention uses cobalt or rhodium-cobalt catalyst to synthesize amino acid derivatives from cyclicamides such as 2-pyrrolidinone and ε-caprolactam, paraformaldehyde and synthesis gas with a high yield using mild pressures and temperatures. The amino acid products may be hydrolyzed to amino dicarboxylic acids and used as monomers to synthesize polyamides.

BACKGROUND OF THE INVENTION

Early attempts were unsuccessfully made to synthesize α-amino acids or derivatives thereof by reacting a Schiff base or a nitrile with carbon monoxide and hydrogen. [Bull. Chem. Soc. Japan 33 (160) 78].

U.S. Pat. No. 3,766,266 to Wakamatsu discloses a method of producing an N-acyl-α-amino acid which comprises holding an aldehyde, an amide of a carboxylic acid and carbon monoxide at a temperature of 10° to 300° C. and a pressure of at least 500 atm. in the presence of a carbonylation catalyst until said N-acyl-α-amino acid is formed.

In *Chem. Comm.* 1540 (1971), Wakamatsu, et al. first disclose a cobalt-catalysed reaction which gives various N-acyl amino-acids from an aldehyde, an amide and carbon monoxide. In this disclosure, while benzaldehyde was used as the starting aldehyde, there was no corresponding α-phenyl-substituted amino acid obtained. Instead of the expected amino acid product, a imine was obtained by a simple "amination" reaction. Dicobalt octacarbonyl was used as the catalyst although the recovery of such metal was not mentioned.

An article by Parnaud, et al., in *Journal of Molecular Catalysis,* 6 (1979) 341–350, discusses the synthesis potential and the catalytic mechanism for the reaction wherein N-acyl-α-amino acids are produced by reacting an aldehyde, CO and an amide in the presence of dicobalt octacarbonyl.

In amidocarbonylation, the aldehyde can be generated in situ from allyl alcohol, oxiranes, alcohols and olefins followed by the reaction with an amide and carbon monoxide to produce an N-acyl-α-amino acid.

A related Patent, U.S. Pat. No. 3,996,288 discloses that when an alcohol or certain of its ester derivatives is held at 50° C. to 200° C. and 10 to 500 atm. in the presence of hydrogen, carbon monoxide, the amide of a carboxylic acid and a carbonylation catalyst, an aldehyde having one more carbon atom than the alcohol or ester is formed in good yield. If the amide has at least one active hydrogen atom on its amide nitrogen, it further reacts with the aldehyde and carbon monoxide to form an N-acylamino acid.

Hirai, et al. discuss a process for combining the transition metal catalyzed isomerization of allyl alcohol to aldehyde and cobalt catalyzed amidocarbonylation to provide a route from allylic alcohols to N-acyl-α-amino acids. See *Tetrahedron Letters,* Vol. 23, No. 24, pp. 2491–2494, 1982.

U.S. Pat. No. 4,264,515 discloses a process for obtaining terminal N-acyl-α-amino acids by a reaction catalyzed by a cobalt carbonylation catalyst wherein the aldehyde is produced in situ from olefins and $CO/H_2$ mixtures. An unsaturated vegetable oil or $C_8$–$C_{30}$ mono olefinic compound is reacted with an amide, carbon monoxide and hydrogen in the presence of a cobalt catalyst. The process is operated in one step and provides for increased selectivity.

In amidocarbonylation, various aldehydes have been disclosed as reactants, however, the potentials of amide reactants in terms of preferred structures or substituents has not been well understood. For example, Wakamatsu in his first report of amidocarbonylation reported that the N-acyl-α-amino acid synthesis can be carried out using a monosubstituted amide. But, Parnaud in J. Mol. Cat. b, (1979) 341–350 reported the attempted reaction of butyraldehyde and N-(α-phenylethyl)acetamide and no norvaline derivative was formed when the reaction was carried out at temperatures between 100° and 180° C.

The synthesis of a cyclic-amidocarboxylic acid requires cyclic amides, such as 2-pyrrolidone and a substituted amide. There is nothing taught or suggested in the art to predict the outcome of this reaction. It was surprising that the reaction selectively produced two major products. Both products can be used as monomers for synthesizing novel polyamides by polymerization.

This invention discloses the synthesis of amino acid derivatives from cyclicamides, a monomer for polyamides such as Nylon 6, paraformaldehyde and syngas. These products could be hydrolyzed to a novel monomer such as an amino dicarboxylic acid.

SUMMARY OF THE INVENTION

This invention concerns a method for synthesizing amino acid derivatives which comprises contacting a mixture of cyclic amides, paraformaldehyde and syngas (carbon monoxide and hydrogen) with a catalyst comprising a bimetallic rhodium-cobalt catalyst optionally in the presence of a solvent at a pressure of at least 500 psi and a temperature of at least 50° C.

DETAILED DESCRIPTION OF THE INVENTION

In the narrower and more preferred practice of this invention amino acid derivatives are prepared from a mixture of cyclic amides, paraformaldehyde, carbon monoxide and hydrogen by a process which comprises contacting said mixture with a catalyst system comprising a rhodium-containing and cobalt-containing compound catalyst in a substantially inert solvent at a temperature of at least 50° C. and a pressure of at least 500 psi until substantial formation of the desired amino acid has been achieved.

The reaction can best be represented by the following Equations I and II:

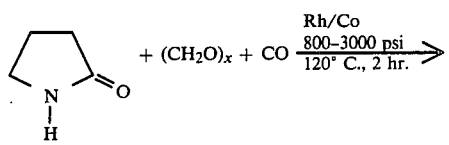

Eq. I

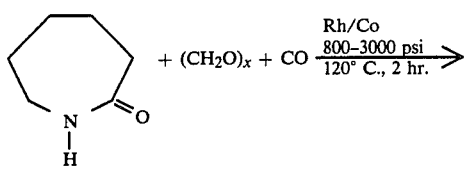

Eq. II

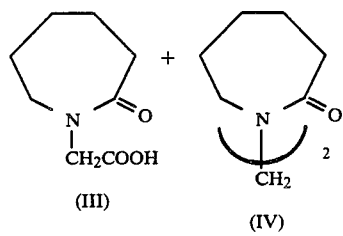

Recovery of the amino acid derivatives from the reaction product can be carried out in any convenient or conventional manner such as by distillation, extraction, filtration, crystallization, etc. In the embodiment of this invention the product was recovered by a simple extraction procedure. The product was identified by HMR.

The catalyst system suitable for the practice of this invention comprises a bimetallic rhodium-cobalt catalyst optionally in a substantially inert solvent.

In the catalyst system of this invention the rhodium-containing compound and cobalt-containing compound are believed to be in complex equilibrium during amidocarbonylation the controlled experiments represented by Examples I-IV show the presence of both Rh and Co is essential. This catalyst system provides advantages over the use of cobalt with respect to the stability and recovery of catalysts.

The rhodium-containing compound may take many different forms. For instance the rhodium could be added in the form of an oxide, a salt of a mineral acid, the salt of a suitable organic carboxylic acid or a carbonyl, hydrocarbonyl or derivative thereof. Compounds which work well in this respect include those where the rhodium is added to the reaction zone as a carbonyl, hydrocarbonyl or substituted carbonyl species wherein the substituted group is triphenylphosphine. The preferred compound is hydridorhodium tris(triphenylphosphine)carbonyl, $HRh(CO)(PPh_3)_3$.

The cobalt-containing compound may take many different forms. For instance, the cobalt may be added to the reaction mixture in the form of a variety of inorganic or organic cobalt salts, or cobalt carbonyls. The cobalt may, for example, be added as a cobalt halide such as cobalt bromide or cobalt chloride, or it may be added as the salt of an aliphatic or aromatic carboxylic acid such as, for example, cobalt formate, cobalt acetate, cobalt butyrate, cobalt naphthenate, and cobalt stearate. The cobalt carbonyl may be tetracobalt dodecacarbonyl or dicobalt octacarbonyl. The preferred cobalt-containing compound is dicobalt octacarbonyl.

The physical parameters which are desirable in the feedstock of this invention for producing the amino acid derivatives are as follows:

The cyclic amides can be described by the structure

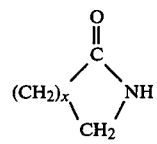

Wherein X=1 to 9

The preferred cyclic amides include 2-pyrrolidinone, ε-caprolactam and γ-valerolactam. Particularly good results are obtained using 2-pyrrolidinone and ε-caprolactom.

Various aldehydes may be used as feedstock in the method of this invention. More specifically aliphatic, alicyclic, aromatic and heterocyclic aldehydes have been used successfully in the method of the invention. Aldehydes giving good yields with suitable amides include paraformaldehyde, formaldehyde, trioxane, acetaldehyde, propionaldehyde, butyraldehyde, phenylacetaldehyde, 2,4-dihydroxyphenylacetaldehyde, indolylacetaldehyde, crotonaldehyde, β-formylpropionaldehyde, β-formylpropionic acid and its esters, β-methylmercaptopropionaldehyde, glycolaldehyde, α-acetoxypropionaldehyde, stearaldehyde, benzaldehyde, furfural, indolaldehyde, adipaldehyde, acrolein and others. Most preferred are paraformaldehyde and formaldehyde.

The carbon monoxide employed need not satisfy particular purity requirements although catalyst contaminants should be avoided if the reaction is intended to continue over an extended period. Particularly in continuous operations, but also in batch experiments, the carbon monoxide and hydrogen gas may also be used in conjunction with up to 10% by volume of one or more other gases. These other gases may include one or more inert gases such as argon, nitrogen and the like or they may include gases that may, or may not, undergo reaction under carbon monoxide hydrogenation conditions, such as carbon dioxide, hydrocarbons, such as methane, ethane, propane and the like, ethers, such as dimethyl ether, methyl ethyl ether and diethyl ether, alkanols, such as methanol, and the like.

As characterized above, this process is operated as a homogeneous liquid phase mixture. The reaction is preferably operated in an inert solvent. Preferred inert solvents are those which permit at least partial dissolution of the cobalt catalyst precursor, the cyclic amide and paraformaldehyde. These are generally polar solvents, of the ester, ether, ketone, amide, sulfoxide or aromatic hydrocarbon type, for example.

Methyl and ethyl acetate are examples of suitable solvents. Other polar solvents are ethers, such as p-dioxane, methyl tertiary butyl ether, methyl tertiary amyl ether or tetrahydrofuran, tertiary amides, such as dimethyl formamide, dimethyl sulfoxide and ethylene carbonate.

The preferred solvent is ethyl acetate.

The amino acids are often insoluble in the solvent phase. This permits separation of the rhodium and cobalt catalyst which may dissolve into the solvent phase, with or without prior acidification.

In all these synthesis in order to achieve a high degree of selectivity the amount of carbon monoxide, aldehyde and cyclic amide present in the reaction mixture should be sufficient to at least satisfy the stoichiometry of the desired formation of amino acid derivatives as shown in Equation I or II above. Excess carbon monoxide over the stoichiometric amount may be present and is desirable.

The quantity of rhodium-containing compound and cobalt-containing compound to be used in the bimetallic catalyst of the invention may vary. The process is conducted in the presence of a catalytically effective quantity of the active rhodium-containing compound and the active cobalt-containing compound which gives the desired product in reasonable yield. The reaction proceeds when employing as little as about 0.01 weight percent, and even lesser amounts of the rhodium-containing compound, along with as little as about 0.1 weight percent of the cobalt-containing compound based on the total weight of the reaction mixture. The upper concentration is dictated by a variety of factors including catalyst cost, partial pressures of carbon monoxide and hydrogen, operating temperature, etc. A rhodium-containing compound concentration of from about 0.01 to about 1.0 weight percent in conjunction with a cobalt-containing compound concentration of from about 0.1 to about 10 percent, based on the total weight of the reaction mixture is generally desirable in the practice of this invention.

Particularly superior results are obtained when the above-noted components of the catalyst system are combined as follows on a molar basis: Rhodium-containing compound to cobalt-containing compound, 1.0:1.0 to 1.0:1000.

The operating conditions may vary over a wide range. The reaction temperature may vary from 25° C. to 300° C. The preferred temperature is from 90° C. to 150° C. The pressure may range from 800 psi to 4000 psi or more. It appears that higher selectivities are obtained when operating at moderate pressures, in the range from 1000 to 3500 psi.

The amidocarbonylation reaction of this invention is best conducted in a carbon monoxide-rich atmosphere, although some hydrogen gas should also be present in order to achieve maximum cobalt catalyst activity. The hydrogen to carbon monoxide molar ratio in the reactor may be varied, for example, within the range from 20:1 to 1:20, but preferably it should be rich in carbon monoxide and the $H_2:CO$ ratio should be in the range of 5:1 to 1:5.

The desired products of this synthesis are amino acids derivatives identified in Equations I and II above as compounds I, II, III and IV. They are identified as the following:

N-(2-pyrrolidone)-2-acetic acid (I)
Bis-N,N'-(2-pyrrolidone)methane (II)
N-(ε-caprolactam)-2-acetic acid (III)
Bis-N,N'-(ε-caprolactam)methane (IV)

Each of these products, including byproducts can be recovered from the reaction mixture by conventional means, e.g. crystallization or filtration.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired amino acid product, and said material may be recovered by methods known to the art, such as filtration, recrystallization distillation, extraction and the like. A fraction rich in the catalyst components may then be recycled to the reaction zone, if desired, and additional products generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analysis, or a combination of these techniques. Analysis have for the most part, been by molar weight; all temperatures are in degrees centigrade and all pressures in pounds per square inch (psi).

The yield of amino acid derivatives in the synthesis using cyclic amides and paraformaldehyde is estimated basis Equation 1 using the formula:

$$\frac{\text{Moles of amino acid derivatives obtained}}{\text{Moles of paraformaldehyde charged}} \times 100\%$$

To illustrate the process of the invention, the following examples are given. It is to be understood, however, that the examples are given in the way of illustration and are not to be regarded as limiting the invention in any way.

EXAMPLE I

A glass-lined stainless steel autoclave equipped with a rocking device, was charged with dicobalt octacarbonyl (0.34 g), paraformaldehyde (2.0 g, 0.066 mole), 2-pyrrolidone (8.5 g, 0.1 mole) and ethyl acetate (15.0 g). The reactor was sealed and flushed with synthesis gas. The system was pressured with 1200 psi of $CO/H_2 = 1:1$ molar ratio and to 2300 psi with CO, resulting in a $H_2/CO$ mixture of approximately 1:3 ratio. The temperature was kept at 120° C. for 2 hours. The resulting homogeneous solution (27 g) was analyzed by H-nmr, showing the following product distribution: (Compound 1:2:3 = 1.4:1.0:1.8 molar ratio)

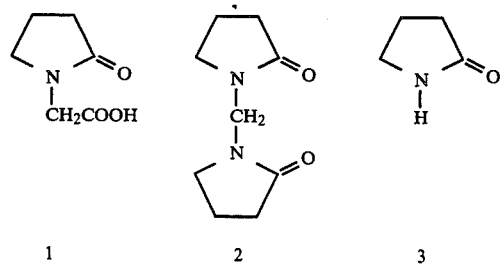

The yields to compound 1 at 59% and to compound 2 at 41% were estimated based on paraformaldehyde charged. The cobalt analysis in product solution showed 3630 ppm (86% recovery).

EXAMPLE 2

The experimental procedures of Example I were employed, using $HRh(CO)(PPh_3)_3$ (0.046 g), $Co_2(CO)_8$ (0.34 g), paraformaldehyde (2.0 g), 2-pyrrolidone (8.5 g) and ethyl acetate (15.0 g). The reaction conditions were 900 psi of CO/H$_2$=1:2 (molar ratio), then 2300 psi with CO (final pressure), 120° C. for 2 hours. A homogeneous deep-red solution was obtained (28.0 g). The H-nmr analysis showed the product distribution as: Compound 1:2:3 =1.0:1.0:1.5 molar ratio.

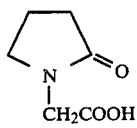 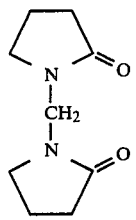 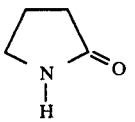

1        2        3

The yields of compound 1 at 50% and compound 2 at 50% were estimated, basis paraformaldehyde charged. The cobalt analysis in solution showed 4800 ppm (>95% recovery).

The high percentage of cobalt recovery was realized using rhodium activated cobalt catalyst.

EXAMPLE 3

A 300 ml magnedrive reactor was charged with HRh(CO)(PPh$_3$)$_3$ (0.023 g, 0.05 mmole), Co$_2$(CO)$_8$ (0.34 g, 1 mmole), ε-caprolactam (11.3 g, 0.1 mole), paraformaldehyde (3.0 g, 0.1 mole) and ethyl acetate (20 g). The operating conditions were ca. 100° C., CO/H$_2$=1:1 molar ratio, 800 psi and 2 hours. The recovery product solution (31.0 g) was analyzed by H-nmr. The crude product solution contained 1.0:2.0 ratio of

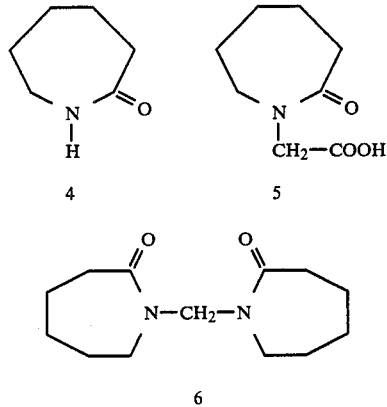

4        5

6 compound 5 to 6 and no significant amount of 4, the starting material.

EXAMPLE 4

A mixture of HRh(CO)(PPh$_3$)$_3$ (0.023 g), Co$_2$(CO)$_8$ (0.34 g), 2-pyrrolidinone (8.5 g, 0.1 mole), paraformaldehyde (3.0 g, 0.1 mole), ethyl acetate (20 g) and H$_2$O (0.90 g) was charged to the 300 ml reactor. The operating conditions were 800 psi, CO/H$_2$ 1:1 molar, 120° C. and 4 hours. The recovered liquid product was analyzed by H-nmr. It contained compound 2 only

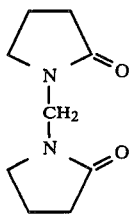

2 with no significant amount of compound 1 or 3. This demonstrates that in the presence of water, the synthesis of compound 2 can be achieved with good selectivity. The presence of water might have detrimental effect on cobalt activity.

What is claimed is:

1. A process for producing cyclic-amido acetic acid derivatives which comprises reacting a C$_4$ to C$_6$ cyclic amide, an aldehyde comprising formaldehyde or paraformaldehyde and synthesis gas with a bimetallic catalyst comprising a rhodium-containing compound and a cobalt-containing compound in a solvent at a pressure of at least 500 psi and a temperature of at least 50° C.

2. The process of claim 1 wherein the aldehyde is paraformaldehyde.

3. The process of claim 1 wherein the cyclic amide is selected from the group consisting of 2-pyrrolidinone, ε-caprolactam and γ-valerolactam.

4. The process of claim 3 wherein the cyclic amide is selected from the group consisting of 2-pyrrolidinone and ε-caprolactam.

5. The process of claim 1 wherein the rhodium-containing compound is selected from the group consisting of a rhodium carbonyl, a rhodium halide, and hydridorhodium tris(triphenylphosphine)carbonyl.

6. The process of claim 5 wherein the rhodium-containing compound is selected from the group consisting of hydridorhodium tris-triphenylphosphine carbonyl, rhodium(III) acetylacetonate and rhodium(III) chloride.

7. The process of claim 6 wherein the rhodium-containing compound is hydridorhodium tris-(triphenylphosphine)carbonyl.

8. The process of claim 1 wherein the cobalt-containing compound is selected from the group consisting of cobalt carbonyls, cobalt halides and cobalt acetate.

9. The process of claim 8 wherein the cobalt-containing compound is selected from the group consisting of dicobalt octacarbonyl, cobalt(II) acetate, cobalt(II) chloride and cobalt(II) bromide.

10. The process of claim 1 wherein the cobalt-containing compound is dicobalt octacarbonyl.

11. The process of claim 1 wherein the solvent is selected from the group consisting of methyl acetate, ethyl acetate and p-dioxane.

12. The process of claim 1 wherein the pressure is from 800 psi to 4000 psi.

13. The process of claim 1 wherein the temperature is from 80° C. to 150° C.

14. The process of claim 1 wherein the carbon monoxide to hydrogen ratio is in the range 5:1 to 1:5.

15. The process of claim 1 wherein the rhodium to cobalt ratio is in the range 1:1 to 1:1000.

* * * * *